(12) United States Patent
Höfer et al.

(10) Patent No.: US 6,314,199 B1
(45) Date of Patent: Nov. 6, 2001

(54) PROCESS AND APPARATUS FOR EXAMINING OPTICAL COMPONENTS, ESPECIALLY OPTICAL COMPONENTS FOR THE EYE AND DEVICE FOR ILLUMINATING CLEAR-TRANSPARENT (75) Inventors: Peter Höfer, Aschaffenburg; Peter Hagmann, Hösbach-Bahnhof; Roland Hauck, Hohenfels; Wolfgang Geissler, Bad Schönborn, all of (DE); Hubert Lutz, Niederwangen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 08/197,100

(22) Filed: Feb. 14, 1994

Related U.S. Application Data (63) Continuation of application No. 07/810,636, filed on Dec. 18, 1991, now abandoned.

(51) Int. Cl.[7] ................ G06K 9/00; G06T 7/00
(52) U.S. Cl. ........................... 382/141; 356/239.2
(58) Field of Search .................. 356/124, 237, 356/239, 239.1, 239.2; 382/8, 141, 142, 149; 250/572; 348/125, 128, 129, 127, 131

(56) References Cited

U.S. PATENT DOCUMENTS

| | | | |
|---|---|---|---|
| 2,332,668 | * 10/1943 | Richards | 359/387 |
| 3,892,494 | * 7/1975 | Baker et al. | 356/237 |
| 3,894,806 | * 7/1975 | Remy et al. | 356/240 |
| 3,988,068 | 10/1976 | Sprague | 356/124 |
| 4,297,032 | * 10/1981 | Temple | 356/239 |
| 4,681,442 | * 7/1987 | Wagner | 356/239 |
| 4,691,231 | * 9/1987 | Fitzmorris et al. | 358/105 |
| 4,733,360 | 3/1988 | Kobayashi et al. | 364/507 |
| 4,815,844 | * 3/1989 | Schmalfuss et al. | 356/239 |
| 4,822,165 | * 4/1989 | Schmalfuss et al. | 356/239 |
| 4,841,139 | * 6/1989 | Schmalfuss et al. | 356/239 |
| 4,943,713 | 7/1990 | Yoshida | 250/223 |
| 5,058,178 | * 10/1991 | Ray | 382/8 |
| 5,179,419 | * 1/1993 | Palmquist et al. | 356/237 |

FOREIGN PATENT DOCUMENTS

| | | | |
|---|---|---|---|
| 3432002A1 | 8/1931 | (DE) | G01B/11/24 |
| 3839682 | 6/1989 | (DE) . | |
| 0063761 | 11/1982 | (EP) | G01B/11/24 |
| 162120 | 11/1985 | (EP) | G01N/21/88 |
| 0249799 | 12/1987 | (EP) | G01N/21/88 |
| 249798 | 12/1987 | (EP) | G01N/21/88 |
| 0359084A2 | 3/1990 | (EP) | B29D/11/00 |
| 0367513 | 5/1990 | (EP) | B29D/11/00 |
| 2433767 | 3/1980 | (FR) | G02B/21/08 |
| 2171812A | 12/1987 | (GB) | G01M/11/02 |
| 2058393 | 4/1991 | (GB) | G02B/21/08 |
| 2257007 | 10/1990 | (JP) | G01B/11/30 |
| 87/04390 | 7/1987 | (WO) | B29D/11/00 |

OTHER PUBLICATIONS

Hoder et al. "Optical Sensor Designs for the detection of cracks in optical materials." Proceedings of SPIE, vol. 1168, 1989, pp. 138–146.*

(List continued on next page.)

Primary Examiner—Jon Chang
(74) Attorney, Agent, or Firm—R. Scott Meece; Robert J. Gorman, Jr.

(57) ABSTRACT

A process and an apparatus for the examination, especially the quality control, of optical components, in which an image of the particular component to be examined is produced and flaws in the imaged article are detected by image analysis, as well as the integration of that examining process into the manufacture of the component. The optical components may be optical components for the eye, such as spectacle lenses, contact lenses, intraocular lenses and the like.

7 Claims, 8 Drawing Sheets

OTHER PUBLICATIONS

MIT 1000 M/Min; Milkroskopiche Oberflächenfehler prüfen! Zur Prüfung von Polymerfolien, Glas, Metallfolien, (Applied Optical Detection).

Bessere Farben UND Schnellere Analyse, Dank Elektronischer Netzhaut, Wild Leitz, Oct. 1989, p. 31.

Bildanalyse, Frank Gottschalk, Oct. 1989, p. 863–862.

Sensor system zur automatischen Prüfung des Füllgutes in universie gelten Tiefziehstreifen, Von H. Gebelmann, 1989 p. 924–930.

Fremd–Körper, Harro HH Höflinger.

Measuring the Radius of Curvature of Hard Contact Lenses and Buttons.

Measurement of soft contact lenses in solution.

Feliss, N.A; Surface Analzer, vol. 25, No. 4. Sep. 1982.

* cited by examiner

PROCESS AND APPARATUS FOR EXAMINING OPTICAL COMPONENTS, ESPECIALLY OPTICAL COMPONENTS FOR THE EYE AND DEVICE FOR ILLUMINATING CLEAR-TRANSPARENT

This application is a continuation of application Ser. No. 07/810,636, filed Dec. 18, 1991, now abandoned.

BACKGROUND OF THE INVENTION

The invention relates to a process and an apparatus for examining optical components, in which an image of the particular component to be examined is produced and flaws in the imaged article are detected by image analysis, and furthermore to an illuminating device for illuminating clear-transparent test objects.

In the manufacture and quality control of optical components, especially optical components for the eye, such as contact lenses, examination is still carried out visually. Attention may be drawn in this connection, for example, to DIN specification 58 223. Visual quality control is a subjective examination only, which depends on the person concerned and is likely to vary depending on the time of day. Consequently there are inevitably shifts in the quality standards of the quality control and it is not possible to achieve adequate reproducibility of the quality of the products. In addition, the possibilities of automation, especially where such components are mass-produced, are considerably handicapped.

Detection of the presence or absence of scratches and the like on the curved surface of lenses in contact lens manufacture by means of an optical projector device and an image-processing device is known from EP 0359 084 A2. The said specification does not, however, disclose how the projector device and the image-processing device are designed so that they can be used for a reproducible quality control, especially in the automatic production of optical components.

Referring to illumination of test objects, the illumination of objects in a microscope by means of "dark field illumination" is known. Such a dark field illumination comprises illuminating an object by means of a light source and an illuminating lens (condenser) in such a manner that the illuminating light beam does not itself enter the ray path of the microscope. Consequently, only the light that is scattered into the ray path by the object is observed.

Illuminating lenses for dark field illumination are known in which there is arranged in the ray path a central diaphragm plate which covers the central portion of the illuminating light beam. It is thus an annular illuminating light beam which strikes a condenser lens and which is collected by the edge parts of the condenser lens in the plane of the object and then directed to the side past the ray path of the microscope lens.

Also known is a so-called "cardioid condenser" in which an annular illuminating light beam is fully reflected at a concave surface at the object side of a first lens. The light beam deflected outwards in this manner strikes an essentially cylindrical generated surface of a second lens. The light beam is again fully reflected by this generated surface. The second lens collects again in the plane of the object the light beam reflected inwards from the edge. From there the light beam, in the shape of a cone, again passes by the ray path of the microscope (Grimsehls Lehrbuch der Physik, 11th edition (1943), vol. 2, published by B. G. Teubner, pages 707–708). These known arrangements are concerned with the illumination of objects in a microscope having an invariable illuminating lens.

SUMMARY OF THE INVENTION

Starting from this state of the art it is an object of the invention to create a process and an apparatus for examining optical components that promote the automation of the examining steps and the manufacture of the optical components. Furthermore, it is another object of the invention to provide an illuminating device for illuminating clear-transparent test objects in order to examine the test objects for flaws, which device permits the flaws to be made clearly detectable. Test objects for such a device may be optical elements, such as lenses, or also spectacle lenses, contact lenses etc. Another problem underlying the invention is especially so to design such an illuminating device that it permits automatic flaw evaluation by observing the test objects using an electronic image-recording device and image-processing.

The problem is solved in the invention as far as the process is concerned by a process in which a two-dimensional high-contrast image of the particular component to be examined is produced and the image area of the flaws which have been made visible is determined, for the purpose of quality control, by comparison with one or more threshold values.

With respect to apparatus, this problem is solved in the invention by providing an optical image-producing device that has a high-contrast-image producing device, and also an image-processing device which comprises an image-recording means with an image sensor that can carry out an area determination of the flaws detected in the high-contrast image.

In the invention an illuminating means is used that renders possible the simultaneous high-contrast representation, in two-dimensional form, of all structures that are of interest on the component to be examined. There is used in combination with this illuminating means an image-recording means with an optical image sensor. The image-recording means may also optionally be provided with a focussing lens with which the high-contrast image can be recorded. The high-contrast image is transmitted to an image-processing device. For that purpose it is advantageous to divide the high-contrast image into image elements (pixels). When a CCD is used as image sensor, this division into image elements is already provided by the design or construction of the CCD. The image elements are converted by means of a converter into digital image signals which can be stored and processed. In this manner an analysis of the structural features of the optical component to be examined (an area determination), and consequently of the flaws detected in the high-contrast image, is possible. For the conversion, advantageously a binary image is first of all produced.

In order to produce the high-contrast image, preferably a dark field illumination of the component to be examined is carried out. With the aid of appropriately scattered light, the component to be examined is illuminated against a dark background, using a camera that optionally contains the image sensor. The image sensor is preferably in the form of a CCD. In this manner a dark field illumination image is taken of the illuminated test specimen. Such an image gives a high-contrast representation of flaws, these flaws appearing as areas on the high-contrast image representation. For example, the flaws in a dark field illumination are represented as light flecks with well-defined areas against a dark (black or grey) background that has no flaws. The flaws may be scratches, holes, air bubbles, fissures, adhering fragments and accumulations of dirt or shrunken areas and the like. The flaws present themselves as areas in the image area. It is also possible, however, to detect errors at the perimeter of the test specimen, which can be represented as two-dimensional shapes. These may be gaps in the perimeter, flash, fissures, fragments adhering to the perimeter, accumulations of dirt and shrunken areas at the perimeter, and perimeter inhomogeneities.

The image areas of the detected flaws can be divided into pixels (image area elements). By means of the number of image area elements (pixels) it is possible to ascertain the extent of a particular flaw or of all the flaws. For this purpose a scanning/counting means may be provided by means of which the pixels can be counted. The number of pixels ascertained for the individual image areas of the detected flaws is compared with a predetermined number of pixels. This predetermined number of pixels is a quality standard which the test specimen has to meet.

For the examination the test specimen can also be divided into different zones for which different threshold values are preset as quality standards. For the examination of a contact lens, for example, different quality standards in the form of preset image areas may be stipulated for the optical zone and the lenticular zone. The quality of the perimeter of the lens can also be determined on the basis of the shape of the two-dimensional image of the perimeter of the contact lens.

Preferably, the invention can be used during the individual production stages of the manufacture of the optical component. For that purpose the flaw detection and quality control according to the invention can be integrated into one or more of the production stages so that there is a continuous automatic quality control during the production of the optical component. For this it is possible to preset appropriate quality standards for the respective production stage so that reproducible quality controls are achieved for each of the production stages in automatic production. The invention can advantageously be used in the quality control of optical components, for example optical lenses, especially optical components for the eye, such as spectacle lenses, contact lenses, intraocular lenses and the like. An automatic final control and, as already explained, also a continuous automatic monitoring of the quality during manufacture of the components, can be achieved in this way.

In the case of contact lens manufacture, for example, both dry examination (examination in air) and wet examination (examination in storage solution) of hydrated contact lenses can be carried out. If the components are stored in transparent containers it is possible to carry out a final control of the components inside the containers.

In the illuminating device already mentioned there are provided a light source and an illuminating lens for illuminating the test objects in dark field illumination. The illumination geometry of the illuminating lens is adjustable to enable adaptation to the test object.

In this manner, by appropriate adjustment of the illuminating lens an illumination adapted to the dimensions and shape of the test objects can be achieved, which permits flaws such as bubbles, fissures or the like to appear as distinct contrasts. The contrasts produced in this manner can be recorded by an electronic image-recording device and evaluated by means of image-processing in order to detect flaws. It has been found that such a representation of flaws in clear-transparent test objects in the form of contrasts is possible by means of dark field illumination, but that it is necessary for this to make the illuminating lens adjustable.

Further developments of the invention form the subject of the dependant claims.

Referring to drawings, the invention is explained in more detail by way of embodiment examples.

DETAILED DESCRIPTION OF THE INVENTION

Figure 1:
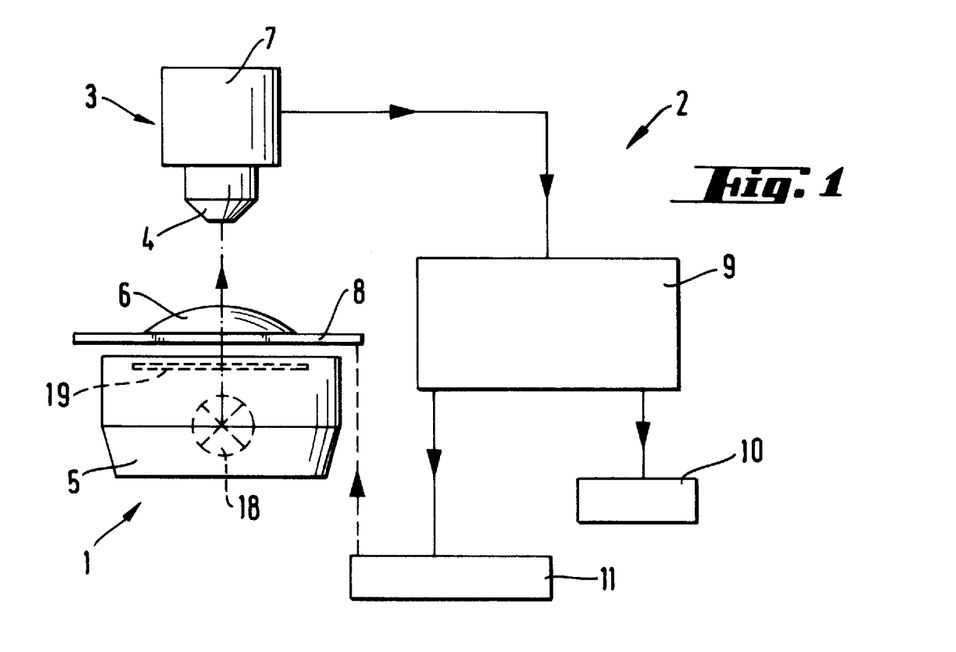
FIG. 1 is a diagrammatic representation of an image analysis device representing one embodiment example of the invention.

FIG. 1 shows an apparatus used for examining optical components. A component 6 to be examined is disposed on a holding and transporting means 8. An illuminating means 1 comprises a high-contrast-image producing device 5, which may take the form of a dark field illumination device. Using a light source 18 of which the light is repeatedly reflected and scattered, the component 6 to be examined is illuminated in front of a dark background 19.

An image-processing device 2 is provided for processing the high-contrast image or dark-field image produced in that manner. The image-processing device 2 comprises an image-recording means 3 with an image sensor 4. This may be, for example, a video camera with the image sensor 4 designed as a CCD.

The video camera may be connected to a monitor, not illustrated, on which the two-dimensional high-contrast image can be made visible. If the image sensor is in the form of a CCD, then, on account of the CCD construction, division of the image into image elements (pixels), for example 500×700, is automatic, that is to say there is automatic image division. Using a reading and converting device 7, the individual image elements of the high-contrast image can be scanned and converted into binary signals, which are then stored and further processed as explained in the following.

Figure 2:
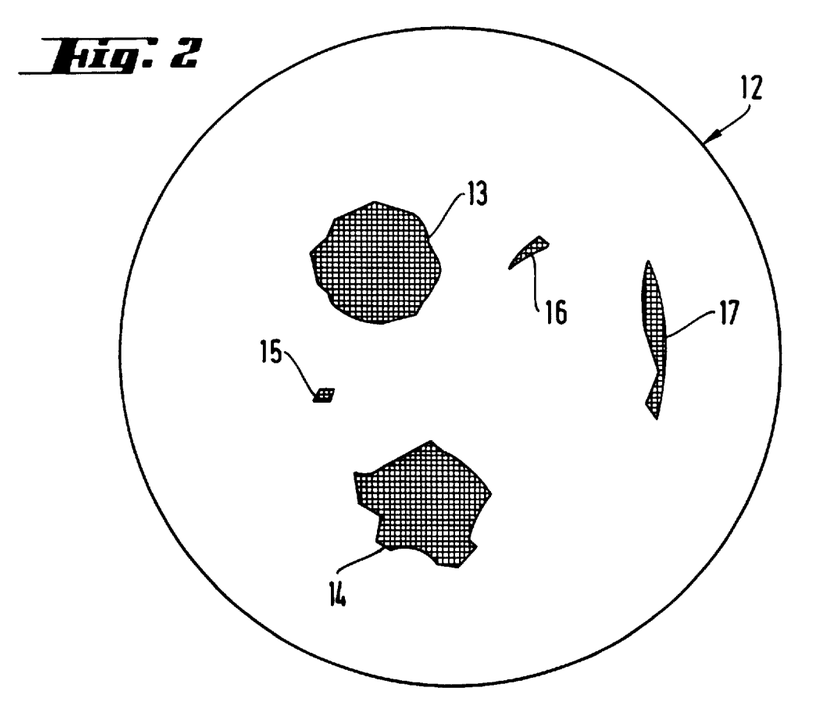
FIG. 2 shows an image of the test specimen produced by the image analysis device of FIG. 1, with flaws reproduced diagrammatically in two-dimensional form.

One embodiment example of a high-contrast image 12 of a test specimen is shown in FIG. 2 in the form of a binary image. This may be, for example, the high-contrast image 12 of a contact lens that is to be examined. Flaws on the surface of the test specimen 6 or enclosed flaws are shown as two-dimensional representations in the high-contrast image 12. These are, for example, the flaws 13, 14, 15, 16 and 17 shown as two-dimensional representations, and may be holes, air bubbles, inclusions, adhering fragments etc.

As shown in FIG. 2, these flaws or flaw areas shown as two-dimensional representations are divided into individual image elements, so-called pixels. Such a division can be effected, for example, using the image sensor 4 (CCD) in cooperation with the reading and converting device 7.

Connected to the device 7 is an image analysis device 9 (image division, counting of pixels, pixel comparison) which ascertains the number of pixels, for example by counting. For that purpose the image analysis device 9 may have an appropriately designed counting means (pixel counter 23 in FIG. 11).

Figure 11:
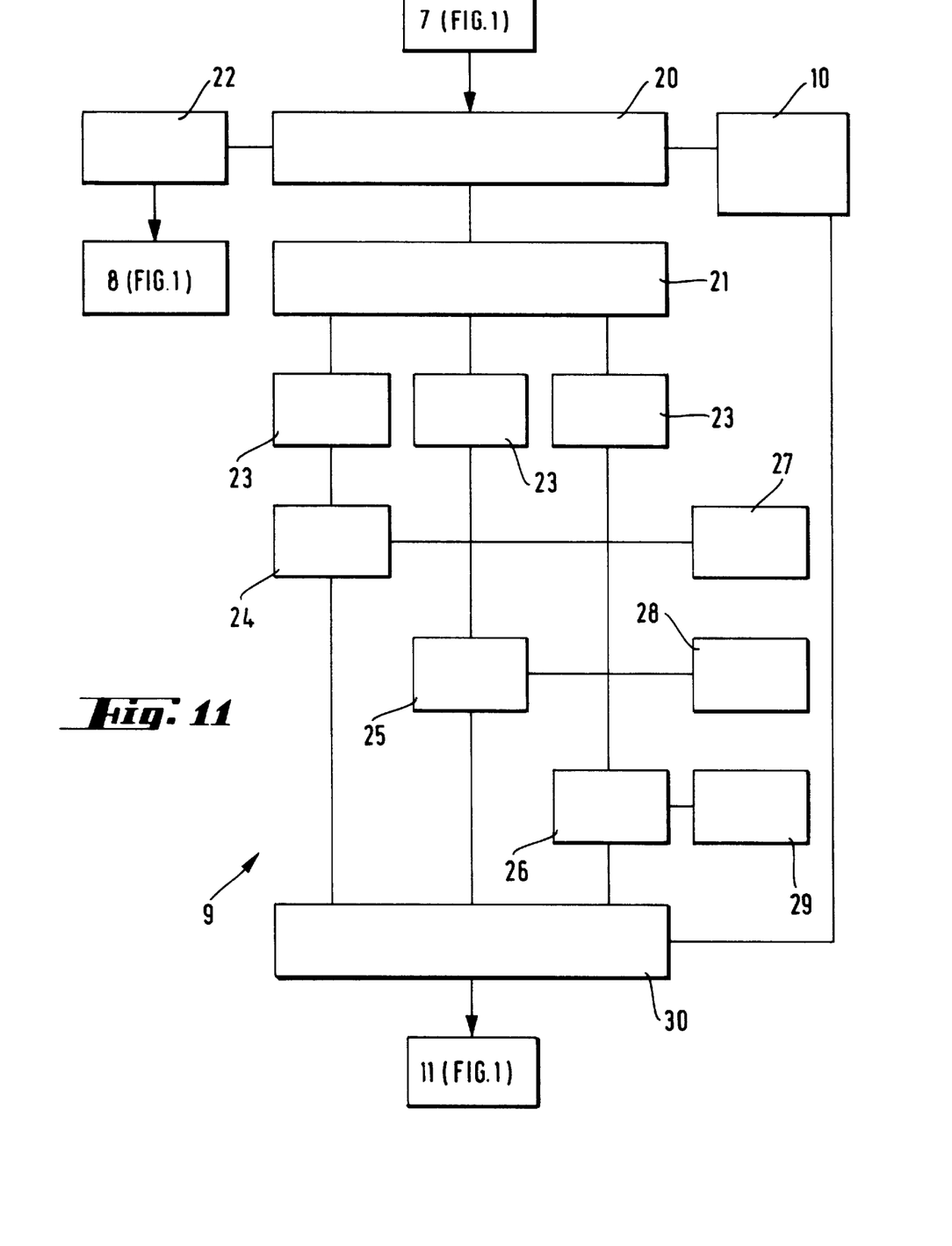
FIG. 11 is a block diagram for an image analysis device shown in FIG. 1.

The mode of operation of the image analysis device 9 is explained with reference to FIG. 11, which is a block diagram of the function units contained in the image analysis device 9.

An image-capture store 20 receives from the reading device 7 (FIG. 1) the image of the component 6 to be examined that has been recorded by the video camera or the image sensor 4 of the image-recording means 3. That image may take the form shown in FIG. 2. In order, for the quality control, to arrange the component 6 to be examined centrally and correctly in the image-producing device 1 and image-processing device 2, an alignment and centering control means 22 is connected to the image-capture means 20. The control means 22 controls the holding and transporting means 8 (FIG. 1) accordingly if the test specimen 6 is not arranged centrally. In order to position the lens in the square field shown in FIG. 3, first of all the perimeter of the lens is detected, which represents the outer boundary of the search field. Upon positioning, the search is then carried out "from the outside inwards".

Figure 3:
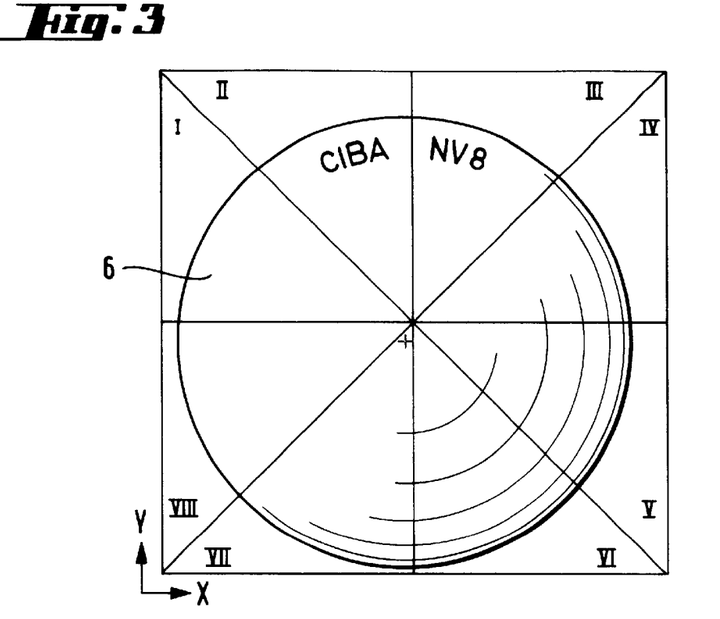
FIG. 3 is a positioning diagram for the image analysis of a test specimen in the form of a contact lens.

Since contact lenses are usually engraved, it is necessary for the examination to cut out the engraving, since otherwise it would cause the indication of a flaw. For that purpose the square field shown in FIG. 3 is divided into eight sectors. In the embodiment example illustrated, the positioning is so carried out that the engraving is arranged half in sector II and half in sector III. One half of the engraving is to the left of the twelve o'clock position and the other half is to the right, the two halves of the engraving being equidistant from the twelve o'clock position. So that the test specimen 6 is positioned correctly, the holding and transporting means 8 may have an x-y displacement means.

If the component 6 to be examined is formed from various zones or parts for which different quality standards suffice or are even required, it is advantageous to divide the recorded image (FIG. 2) of the component 6 to be examined into corresponding zones.

Figure 4:
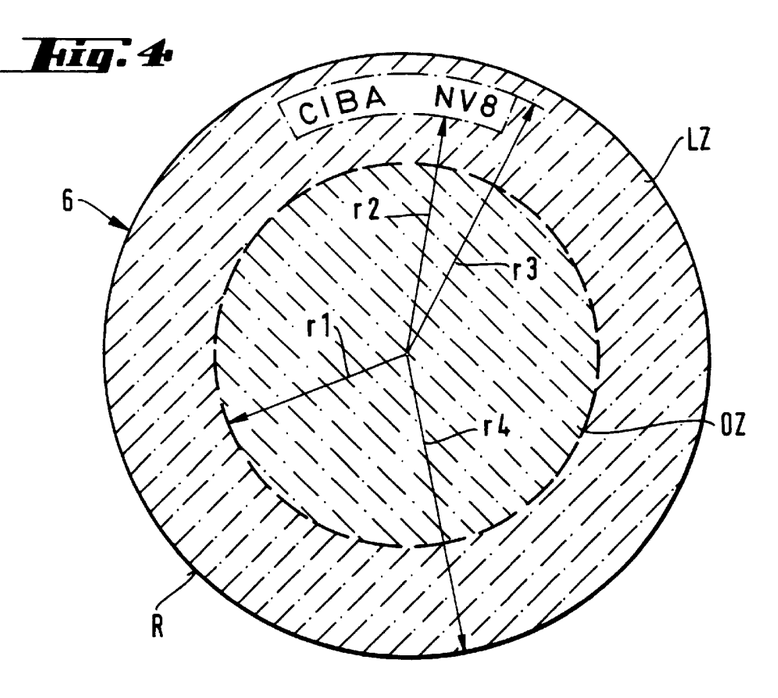
FIG. 4 shows a zone division of a test specimen in the form of a contact lens.

FIG. 4 is a diagrammatic representation of such a division into zones, for example for a contact lens. One region, which is defined by a radius r1, forms an optical zone OZ of the contact lens. The radii r2 and r3 define a writing zone, which is to be blanked out, in the sector with the engraving.

A lenticular zone LZ is defined by a region between radii r1 and r4 and the perimeter R of the lens is defined by the radius r4.

Different flaw thresholds can be set for the optical zone OZ and the lenticular zone LZ, the flaw threshold for the optical zone OZ having to be set lower than the flaw threshold for the lenticular zone LZ. A perimeter error threshold can also be set for the perimeter R; for example, the longitudinal and/or transverse dimensions may not be greater than 50 $\mu$m. The flaw threshold can in the case of the invention, however, be set even lower, for example at 20 $\mu$m. This applies also to the flaw thresholds in the optical region OZ and in the lenticular region LZ. The flaw threshold is set in accordance with how high the quality of the contact lens or of the component 6 to be examined is to be.

Figure 5:
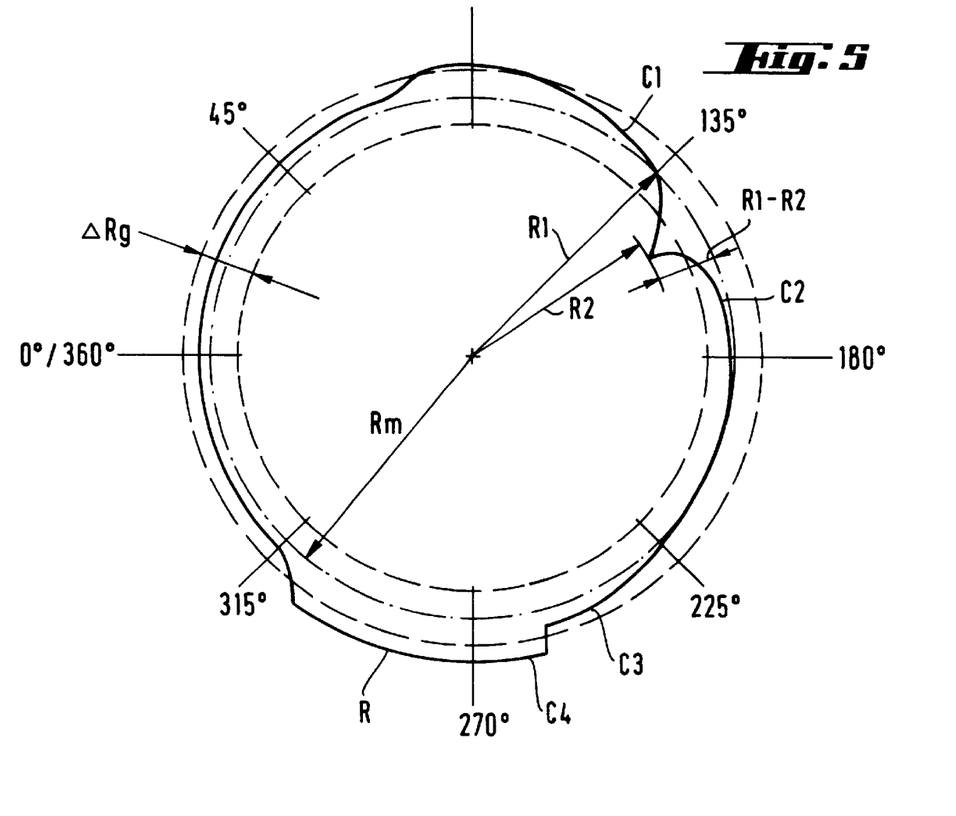
FIG. 5 shows a detection diagram for perimeter flaws in a test specimen in the form of a contact lens.
Figure 6:
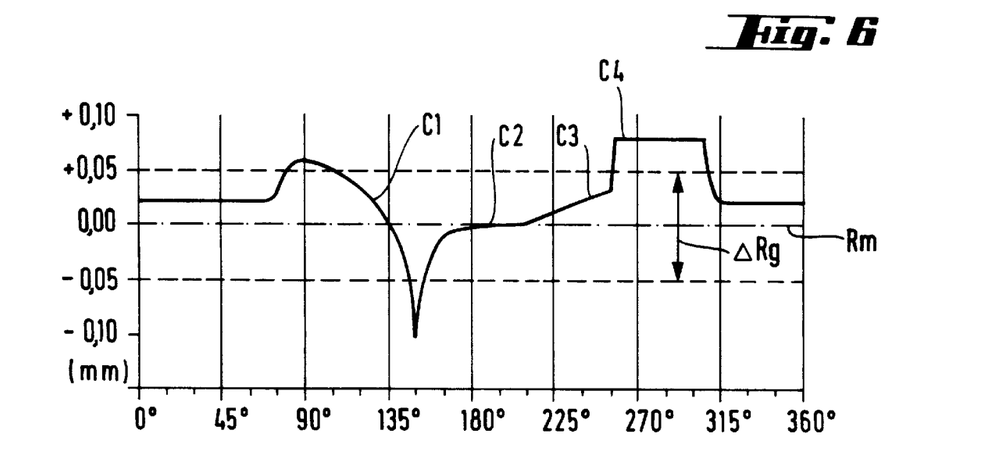
FIG. 6 is a graph representation of the perimeter flaws detected in accordance with FIG. 5.

Whereas, for the two-dimensional zones of the image, appropriate associated flaw thresholds are set, flaw detection for the contact lens perimeter R can be carried out in accordance with the principle illustrated in FIGS. 5 and 6. For this various criteria can be taken into consideration individually or all together. One criterion may be whether the radius at a particular perimeter position deviates from a mean radius $R_m$ beyond a preset radius deviation $\Delta Rg/2$ or not. A further criterion for consideration may be whether those excessive radius deviations as a whole exceed a certain threshold or not. Finally, a further criterion that may be examined is whether the curve shape of the perimeter markedly deviates from a circular shape or not, as is illustrated, for example, between the two curve portions $C_1$ and $C_2$ resp. between the curve portions C3 and C4 in FIG. 5. FIG. 6 shows, for example, that approximately at 150° there is a pronounced radius deviation. This is shown by R1–R2 in FIG. 5. It is also possible to see in FIG. 6 the pronounced deviation of the perimeter from the circular shape between the curve portions C3 and C4. Also in FIG. 6, a pronounced radius deviation is recognisable in the region from approximately 260° to 300°.

The aforesaid flaws can be detected in the image analysis device 9 (FIG. 1) with the aid of a storage means 21 (FIG. 11), in which the zone division shown in FIG. 4 is set, in conjunction with threshold value stores. For example, a threshold value store 27 is provided for the optical zone OZ, a threshold value store 28 is provided for the lenticular zone LZ and a third threshold value store 29 is provided for the perimeter R. There are associated pixel counters for the corresponding zones. The pixel counters, which indicate values for the sizes of flaw in the respective zones, deliver those values to comparators 24, 25 and 26, which are connected to the described associated threshold value stores 27, 28 and 29. The result of the comparison may be filed in an intermediate store 30 for the respective zones and optionally reproduced, together with the recorded image in the image-capture store 20, on a monitor 10.

Furthermore, depending on the respective comparison results of the comparators 24, 25 and 26, a selector 11 (FIG. 1) is actuated either directly or by way of the intermediate store 30. The selector 11 is connected to or is in operative connection with the holding and transporting means 8. This is illustrated diagrammatically by a broken line in FIG. 1. The component 6 to be examined is left on the holding and transporting means 8 when according to the comparison result it satisfies the quality requirements. The component 6 to be examined is then transferred to the next processing station. If the component 6 does not satisfy the quality requirements, it is removed from the holding and transporting means 8 by the action of the selector 11.

Figure 12:
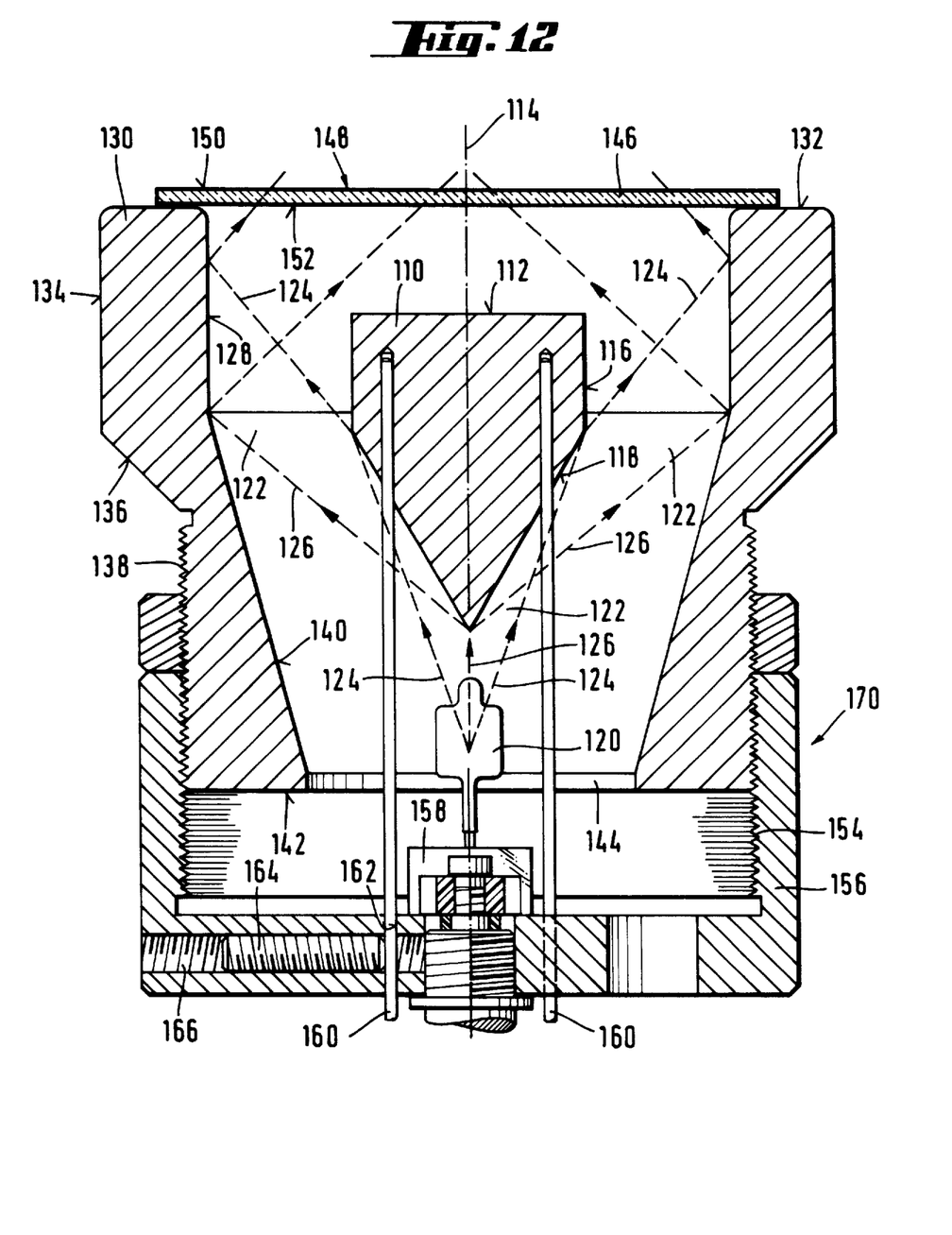
FIG. 12 shows a longitudinal section of an illuminating device for illuminating clear-transparent test objects in dark field illumination.

An embodiment of the device for illuminating the test object, e.g. for illuminating the contact lens, is shown in FIG. 12. In this figure, reference sign 110 indicates a central first reflector body. The first reflector body 110 has a planar, upper end face 112. The upper end face 112 extends at right angles to a system axis 114. Adjacent to the end face 112 the reflector body 110 has a cylindrical generated surface 116 which is coaxial with the system axis 114. On the underside, the reflector body 110 forms a convex-conical first reflector 118. The cone axis of the reflector 118 coincides with the system axis 114.

A light source 120 is arranged below the reflector body 110 on the system axis 114. From the light source 120 a central light beam 122 strikes the convex-conical first reflector 118. The light beam 122 is fanned out radially by the first reflector 118. In the drawing, the edge rays 124 and the central ray 126, which extends along the system axis 114, of the light beam 122 are shown before and after reflection at the first reflector 118.

The radially fanned-out light beam 122 strikes a second reflector 128. The second reflector 128 is concave-cylindrical and coaxial with the system axis 114. The second reflector 128 is disposed on a second reflector body 130. The second reflector body has an annular, planar end face 132. The cylindrical reflector 128 is adjacent on the inside to the end face 132. On the outside the reflector body 130 has, adjacent to the end face 132, a cylindrical generated surface 134 which is coaxial with the reflector 128. Adjacent to the cylindrical generated surface 134 the reflector body 130 has a conical portion 136. Adjacent to the conical portion 136 is a cylindrical portion 138 which is provided with an external thread. On the inside there is adjacent to the cylindrical reflector 128 a conical portion 140. At the bottom, the reflector body 130 has a lower end face 142 having a central aperture 144. The light source 120 projects through that aperture 144 into the interior of the reflector body 130.

On the upper end face 132 of the reflector body 130 there is a clear-transparent plate 146 which, with its flat upper side, forms a support 148 for the test objects. The supporting plane defined by the support 148 is perpendicular to the system axis 114 and accordingly parallel to the end face 112 of the first reflector body 110. The plate 148 is provided at the top and bottom with reflection-reducing layers 150, 152. The concave-cylindrical second reflector 128 reflects the radially fanned-out light beam 122 in such a manner that it is collected almost glancingly in the middle of the support 148 in one light spot.

The second reflector body 130 is screwed, by the portion 138 provided with an external thread, into a pot-shaped housing member 156 provided with an internal thread 154. The housing member 156 carries on the inside, on the system axis 114, a base 158 for the light source 120. In addition, support rods 160 are mounted in the base of the pot-shaped housing member 156, which rods support the first reflector body 110. The support rods 160 are guided through aligned apertures in the base of the housing member 156, and through a transverse bore 162 of clamping screws 164. The clamping screws 164 are seated in radial threaded bores 166 in the base of the housing member 156 between the said aligned apertures. The clamping screws 164 can be released. The support rods 160 and consequently the first reflector body 110 are then vertically displaceable relative to the pot-shaped housing member 156. It is thus possible to adjust the reflector body 110 in relation to the light source 120. The housing member 156, the light source 120 and the first reflector body 110 form a coherent subassembly 170 which, by means of the internal thread 154 and the externally threaded portion 138 of the second reflector body 130, is displaceable as a whole, in the direction of the system axis 114, relative to the second reflector body 130 and thus to the second reflector 128 and to the support 148 (or vice versa).

By means of this displacement, firstly, the light spot produced in the support plane is adapted to the dimensions of the test objects, and secondly the apparatus can be so adjusted that optimum contrast is provided for the detection of flaws.

The reflectors 118 and 128 may be specular. The surfaces of the first and of the second reflector 118 and 128 may, however, alternatively be designed to be partially diffuse-reflecting.

An alternative solution may consist in the light source being a barretter-ring light. The adjustability of the illumination geometry in that case may consist in the radiation characteristic of the barretter-ring light being adaptable to the geometry of the test object.

Figure 7:
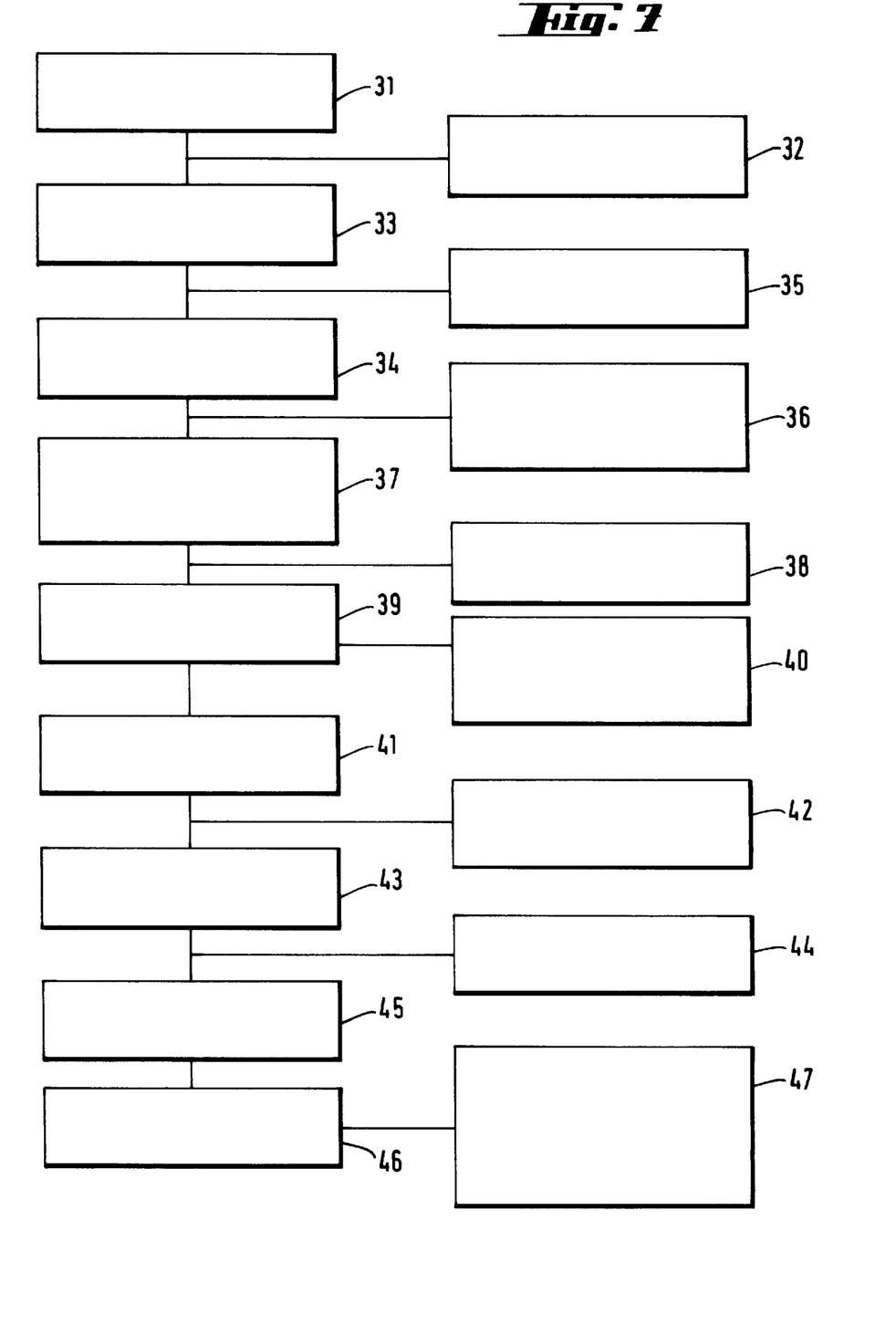
FIG. 7 is a diagrammatic representation of various production stages in the manufacture of a contact lens with integrated automatic examining steps.
Figure 8:
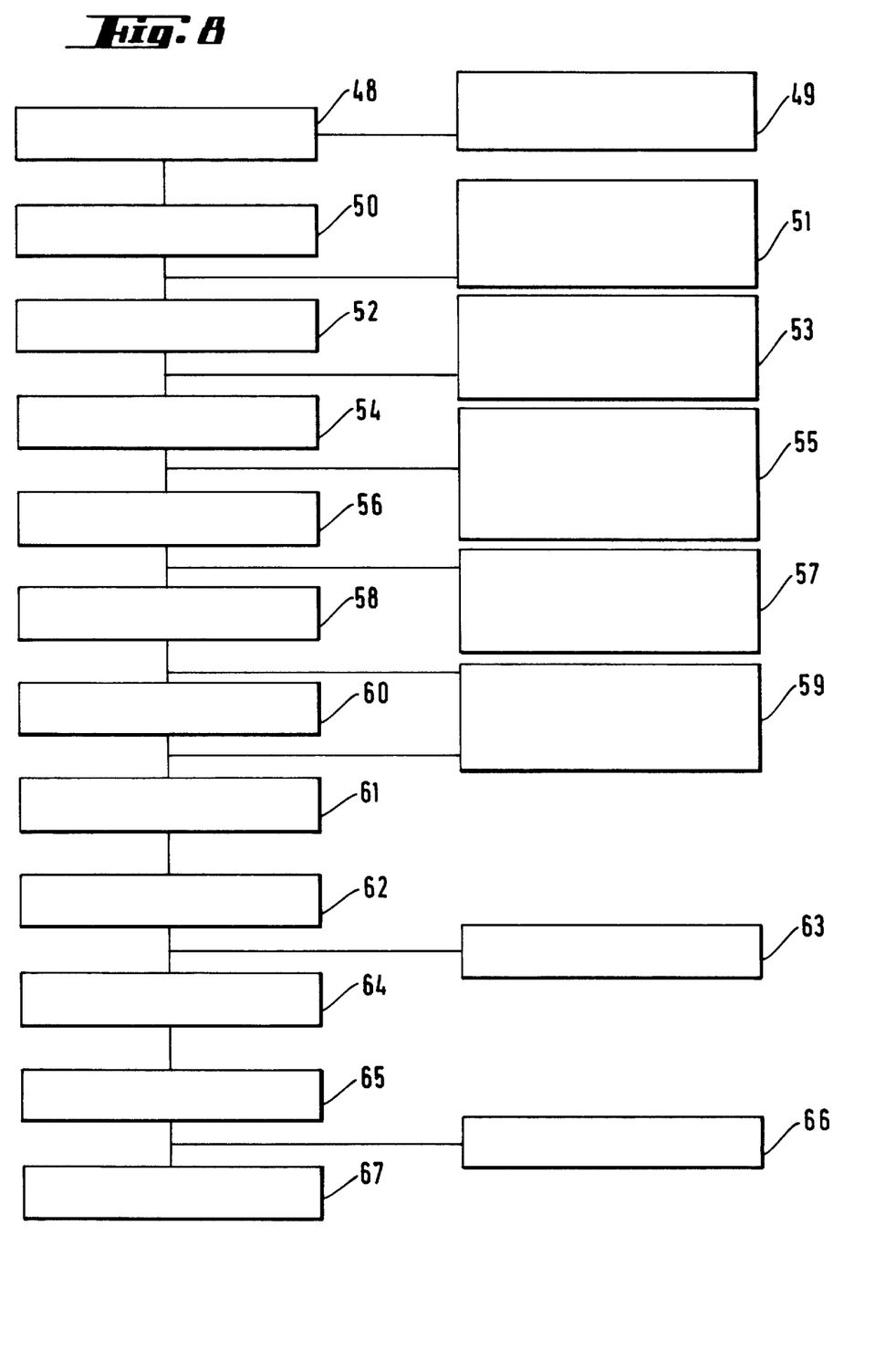
FIG. 8 is a diagrammatic representation of various production stages of another manufacturing process for contact lenses with integrated automatic examining steps.

Referring to FIGS. 7 and 8, two different manufacturing processes for contact lenses are used to show how the image analysis according to the invention combined with other image-processing operations can be intregated into the manufacturing process at different production stages or steps, so that automation of the entire manufacture of the contact lens is achieved.

In FIG. 7 a so-called full mold process, which comprises molding the contact lens, is shown in its individual stages, with integrated automatic examination using the image analysis according to the invention. Full mold processes are known (e.g. EP 0 367 513 and WO 87/04390).

In a production stage 31, the mold inserts (optical tools), which consist of high-grade metals/alloys, are produced, for example, by machining. Even at this stage a first examining step 32 can be carried out using image analysis. This examining step can examine the surface quality of the mold inserts and the geometry of the mold inserts. Then, in a step 33, the mold inserts are inserted into an injection molding tool. At this stage, too, an optical examination can be carried out using image analysis in an examining step 35 for examining the surface quality and the assembly dimensions.

Following this there is the manufacture of the plastics molds, that is to say the two mold halves (molds), in which the contact lens is to be produced by molding (production stage 34). Here, too, an examining step 36 by image analysis can be incorporated, so that the surface quality, the geometry (distortion and the like) and freedom from dust of the manufactured mold halves can be checked. Following this, the polymerisation mixture for the contact lens material is dispensed and the two mold halves are closed in a production stage 37. An examining step 38 can also be incorporated here, it being possible to determine whether the closure is correct and whether air bubbles are present using the illustrated image analysis.

There then follows, in a production stage 39, the polymerisation of the contact lens material enclosed by the two mold halves. During this it is possible in an examining step 40 to monitor in a closed mold that is transparent not only the progress of the polymerisation but also the polymerisation shrinkage of the polymerised material and a suitable adjustment of the two mold halves in that respect. Where appropriate, the adjustment of the two mold halves to compensate for the polymerisation shrinkage can be controlled as a function of the result of the image analysis and the ascertained polymerisation shrinkage.

In a further production stage 41, the two mold halves are opened. It is possible within the scope of an integrated examining step 42 to carry out an intermediate inspection here with respect to crude flaws, such as fissures, gaps etc. in the lens body.

Figures 9, 10:
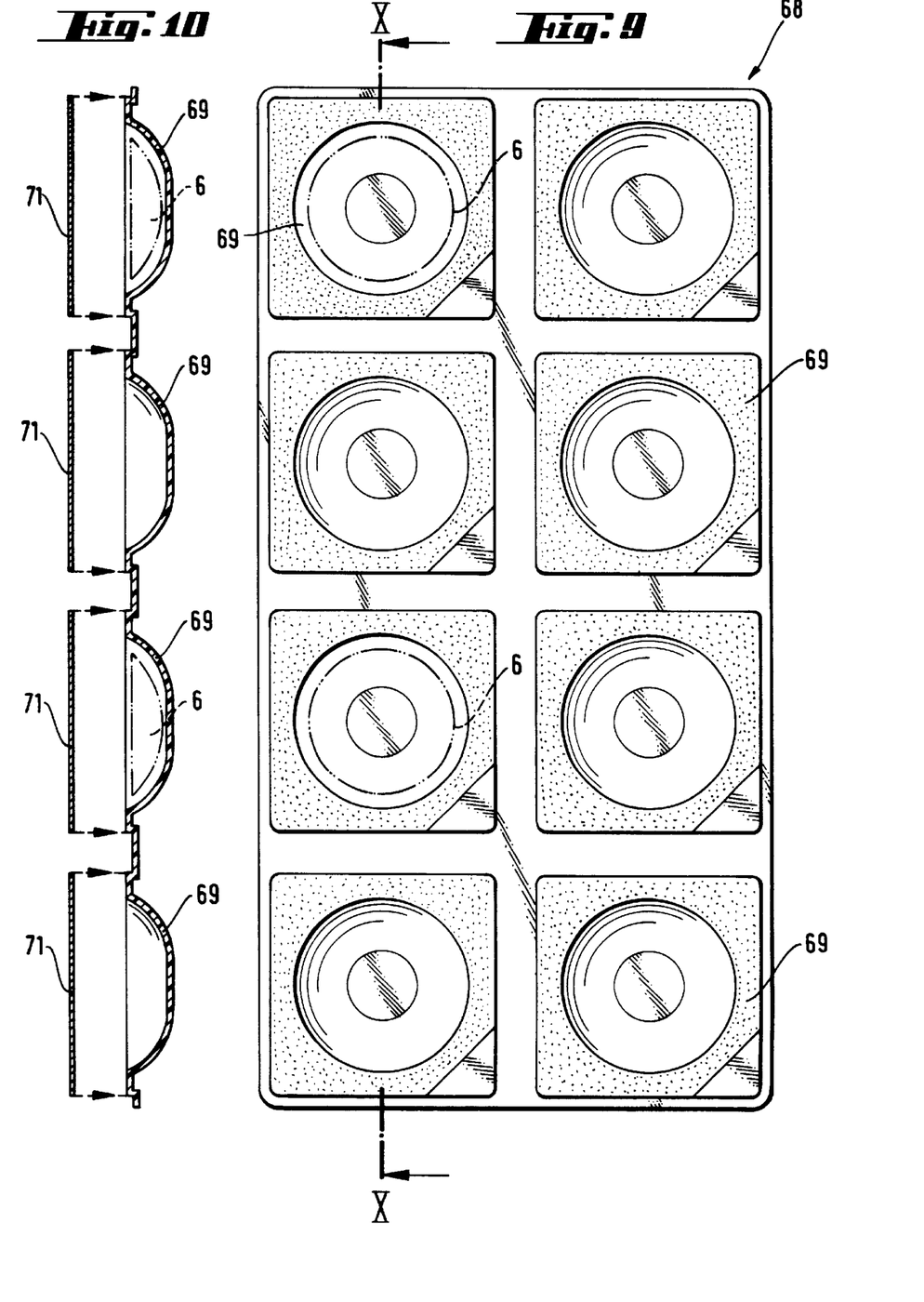
FIG. 9 shows in plan view a packaging, especially for contact lenses, suitable for a final examination using the process according to the invention.
FIG. 10 is a sectional representation of the packaging shown in FIG. 9.

In the subsequent production stage 43, the contact lens is removed from the mold, and dry examination can be carried out on the contact lens in an examining step 44 using the illustrated image analysis. This may be followed in a production stage 45 by the hydration of the lens body. In a further production stage 46 the lens (dry or hydrated) is introduced into small glass vessels or so-called foil packs 68, which are illustrated in FIGS. 9 and 10.

Then, in an examining step 47, it can be checked whether the lens has been introduced into the storage container 69. This is effected in the course of a so-called presence check. Whether the level of liquid in the storage container is correct can also be checked. In addition, the cleanliness of the storage liquid and of the lens itself can be inspected. Also, lens quality and refractive power can be subjected to a final examination. The examinations explained in the examining step 47 can be carried out using the above-described image analysis. The containers (FIGS. 9, 10) are then sealed with covering sheets 71 by welding.

FIG. 8 shows a turning process, which can also be used to produce a contact lens. In this turning process, in a production stage 48 a button is cut off from a rod of contact lens material and inserted into a clamping chuck of a lathe. Automatic lathes are known. Reference is made in this connection, for example, to German Patent Specification 31 10 624. In an examining step 49, for example the button can be examined with respect to material inclusions and to its dimensions (trimmed size) using the above-described image analysis. In a production stage 50, an inner curve is produced in the button by turning by means of a turning tool in the automatic lathe. In a subsequent examining step 51, by means of image analysis the turned form and the surface quality, and optionally also the geometry, for which also a known Moiré process can be used, can be examined.

In a further production stage 52 the inner curve is polished. If desired, the polished form, the surface quality and once again the geometry of the inner curve may be checked in an examining step 53.

The button is then cemented onto a spindle of the automatic lathe in a production stage 54. The button is cemented onto the spindle by its inner curve. Here, too, the quality and the dimensions of the layer of wax used to cement the button to the spindle can be checked in an examining step 55 using optical image analysis, as can also the centering, and the summit of the curve can be ascertained.

Subsequently, the outer curve is turned in a further production stage 56. The turned form, the geometry and the centre thickness of the finished lens may be examined in an examining step 57.

The outer curve is then polished in a production stage 58. In an examining step 59, the polished form, the geometry and the centre thickness of the contact lens can then be checked. The examining step 57 can in that case be omitted.

In a production stage 60, the contact lens is detached from the cap of the automatic lathe. In a production stage 61, the perimeter of the contact lens is machines. In a following production stage 62 the contact lens is cleaned. Following cleaning of the contact lens there may be an examining step 63 in which a dry examination of the contact lens is carried out by image analysis (e.g. FIG. 1).

There then follows, as production stage 64, the engraving of the contact lens. In this stage, for example the engraving visible in FIGS. 3 and 4 is made in the contact lens body. A surface treatment of the contact lens then follows as production stage 65. This has, in particular, the advantage that the surface of the lens is made wettable for the lacrimal fluid. The wettability can then be examined in an examining step 66 also by image analysis (e.g. FIG. 1). By means of image analysis it is possible to ascertain whether droplets form on the surface of the lens or whether the whole of the lens surface is wet with liquid.

In a further production stage 67, the lens is inserted into a container, for example into foil packs (FIGS. 9, 10). An examining step corresponding to examining step 47, as in the full mold process shown in FIG. 7, may then follow, after which the covering sheets are welded onto the containers.

From the above explanation, especially in connection with FIGS. 7 and 8, it can be seen that complete monitoring and at the same time 100% automation can be achieved in the production of optical components using optical image analysis. This applies especially to the manufacture of contact lenses. By this means the desired product quality is guaranteed by continuous monitoring (in-process control) of the entire production run, so that it may be possible to dispense with a final control. Such monitoring is advantageous especially for contact lenses (disposable lenses) that are to be produced in large numbers. The quality control guaranteed by the invention is governed by a presettable quality standard and is consequently a reproducible and objective quality control.

What is claimed is:

1. A process for examining a transparent optical component, in which an image of the entire component to be examined is produced, the process comprising the steps of:
   (a) dark field illuminating the entire optical component, thereby producing at one time a two-dimensional high-contrast image of the whole component;
   (b) recording at one time the entire two-dimensional high-contrast image of the whole component;
   (c) displaying at one time the entire two-dimensional high-contrast image of the whole component;
   (d) determining the image area of flaws in said component; and
   (e) comparing said flaw image area with one or more threshold values during image analysis.

2. A process according to claim 1, wherein the image area of the flaws detected is divided into pixels and the pixels are counted, and the number of pixels ascertained is compared with a predetermined number of pixels.

3. A process according to claim 1, wherein the detection of flaws is carried out in one or more production stages of the manufacture of the component.

4. A process according to claim 1, wherein the detection of flaws is carried out in the manufacture of optical components for the eye.

5. A process according to claim 1, wherein different threshold values are set as quality standards for different zones of the component to be examined.

6. A process according to claim 5, wherein said transparent optical component is a contact lens and different threshold values are set as quality standards for the optical zone, the lenticular zone and the perimeter of the lens.

7. An apparatus for examining a transparent optical component, comprising:
   an optical image-producing device being provided with a dark-field illumination means, the dark-field illumination means illuminating the component and the optical image-producing device receiving the light transmitted through the component the image-producing device recording a two-dimensional high-contrast image of the whole component to be examined at one single time and then displaying said image; and
   an image-processing device having an image-recording means with an image-sensor for area determination of the flaws detected in the high-contrast image wherein the illuminating device for illuminating transparent optical components comprises a light source and a reflector for illuminating the test objects in dark field illumination, and wherein the reflector is adjustable to enable adaptation to the test object
wherein
- (a) a first reflector body is arranged below a support having a support plane for test objects,
- (b) the first reflector body has an end face essentially parallel to the supporting plane of the support, which end forms a background for the test objects,
- (c) the first reflector body furthermore has, remote from the said end face, a convex-conical first reflector of which the cone axis coincides with a system axis which extends at right angles to the end face,
- (d) the light source is arranged on the system axis and
- (e) a second reflector body having a concave annular reflector is arranged coaxially with the system axis wherein the light source is combined with the first reflector in a sub-assembly which is displaceable along the system axis relative to the second reflector body and to the support.

* * * * *